United States Patent [19]

Baker et al.

[11] 3,948,972

[45] Apr. 6, 1976

[54] ESTERIFICATION OF NITROBENZOIC ACIDS

[76] Inventors: James Albert Baker, 5 Dove House Crescent, Farnham Royal, Slough, Buckinghamshire; Antony Gray, 723 Bath Road, Taplow, Maidenhead, Berkshire; John Francis Benford, 14 Hanwood Close, Woodley, Berkshire, all of England

[22] Filed: Nov. 12, 1973

[21] Appl. No.: 414,891

Related U.S. Application Data

[63] Continuation of Ser. No. 187,159, Oct. 6, 1971, abandoned.

[52] U.S. Cl............................................ 260/471 R
[51] Int. Cl.$^2$........................................ C07C 76/02
[58] Field of Search ............................... 260/471 R

[56] References Cited
UNITED STATES PATENTS
3,013,051   12/1961   Richter .............................. 260/471

*Primary Examiner*—Vivian Garner
*Attorney, Agent, or Firm*—William A. Drucker

[57] ABSTRACT

Glycerol esters of nitrobenzoic acid are prepared by heating a mixture of a nitrobenzoic acid and glycerol in the presence of a catalytic quantity of an acid esterification catalyst which is soluble in the reaction medium at the reaction temperature. An entraining liquid having a boiling point above 100°C is also present in the raction mixture. The reaction mixture is heated to a temperature above 100°C so that liberated water is separated by azeotropic distillation. Surprisingly good yields are obtained using these reaction conditions.

9 Claims, No Drawings

ESTERIFICATION OF NITROBENZOIC ACIDS

This is a continuation of application Ser. No. 187,159 filed Oct. 6, 1971, now abandoned.

The present invention relates to the preparation of glycerol esters of nitrobenzoic acids, especially p-nitrobenzoic acid.

As far as we are aware, it has not been commercially feasible prior to the present invention to directly esterify nitrobenzoic acids with glycerol. The methods described in the literature for producing glycerol esters of nitrobenzoic acids all rely upon the reaction of glycerol with a nitrobenzoyl chloride in the presence of a base such as pyridine. Most of said prior art processes are directed at preparing specific isomers of glycerol mono-p-nitrobenzoate and involve the use of blocking groups to ensure that only one of three hydroxy radicals of glycerol is available for esterification. Examples of such esterifications are as follows:

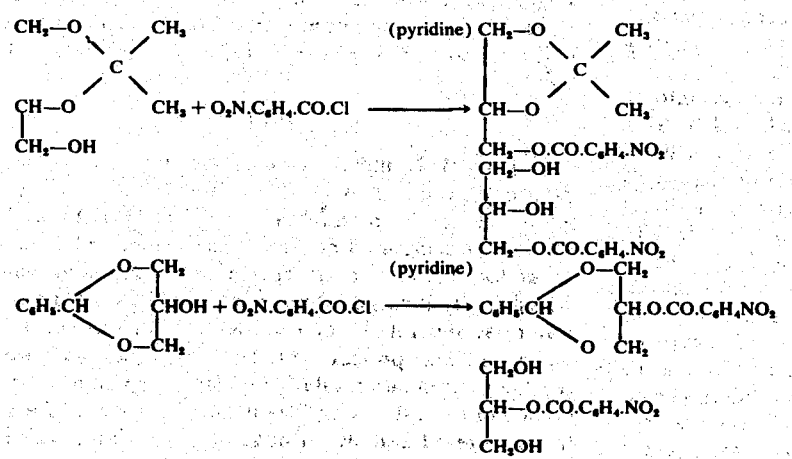

The present inventors have now found surprisingly that glycerol esters of nitrobenzoic acids can be prepared by direct esterification of glycerol with nitrobenzoic acid in high enough yield to justify commercial scale operation provided that:
a. the reaction temperature is above 100°C;
b. the reaction is carried out in the presence of an acid esterification catalyst which is soluble in the reaction mixture at the reaction temperature; and
c. the reaction is carried out in the presence of an entraining liquid having its boiling point above 100°C.

If any one of said process requirements is not fulfilled the esterification is unlikely to proceed and if it does proceed will not do so with a commercially viable yield of ester. In experiments conducted by the present inventors it was found that the direct esterification occurred readily and in high yield when glycerol and a nitrobenzoic acid were heated together at reflux temperature (atmospheric pressure) in the presence of sulphuric acid as catalyst and toluene as entraining liquid. However, esterification failed to take place when orthophosphoric acid was used instead of the sulphuric acid, the reaction conditions being otherwise identical. Similarly, esterification did not take place either when using sulphuric acid and toluene at temperatures below 100°C or when using carbon tetrachloride instead of toluene and reaction conditions otherwise identical to the successful esterification.

According to the present invention, therefore, there is provided a method of esterifying a nitrobenzoic acid with glycerol comprising heating at a temperature of at least 100°C a mixture of the nitrobenzoic acid and glycerol in the presence of (a) a catalytic quantity of an acid esterification catalyst, which is soluble in the reaction mixture at the reaction temperature and (b) an entraining liquid having its boiling point above 100°C to separate liberated water by azeotropic distillation.

The product of the method of this invention usually will be mono-and/or di-ester obtained by esterification with a nitrobenzoic acid of one or both terminal hydroxyl groups of glycerol. However, the corresponding tri-ester may be prepared by appropriate selection of reactant ratio. The proportion of mono-to di-ester will vary with the relative proportions of acid and alcohol in the reaction mixture. Thus, as might be expected from conventional direct esterification of acids with polyhydric alcohols, a large excess of acid promotes formation of the diester whereas a large excess of glycerol promotes formation of the mono-ester. However, it has surprisingly been found that the method of the present invention strongly favours formation of the mono-ester when the glycerol is present in a relatively small excess. An esterification product consisting of more than 90% mono-ester and the remainder di-ester can be obtained by using a molar ratio of glycerol to nitrobenzoic acid of 3 or more : 1. At a molar ratio of about 4 : 1 95% or more of the esterification product is constituted by the mono-ester. Such products are particularly useful when the nitrobenzoic acid is p-nitrobenzoic acid because they can be reduced in known manner to mixtures of glycerol mono- and di-para-aminobenzoates containing a very high proportion of the mono-aminobenzoate, which mixtures constitute excellent sun-screening agents.

According to a preferred embodiment of the present invention therefore there is provided a method of obtaining glycerol mono-para-nitrobenzoate which comprises heating at a temperature of at least 100°C a mixture of glycerol and para-nitro-benzoic acid in a molar ratio of at least 3:1 in the presence of (a) a catalytic amount of an acid esterification catalyst which is soluble in the reaction mixture at the reaction temperature and (b) an entraining liquid having its boiling point above 100°C to separate liberated water by azeotropic distillation. As stated previously, the esterification product may contain up to 10% of di-ester and the product usually will be used without separation of said di-ester. The presently preferred acid esterification catalyst for use in the method of the present invention is sulphuric acid although other acid esterification catalysts soluble in the reaction mixture at the reaction temperature, e.g. toluene sulphonic acids, may be used. It has been found that the rate of esterification increases with the amount of sulphuric acid within the catalytic range but care must be taken to use insufficient sulphuric acid for reaction with the glycerol. Suitably, the sulphuric acid is present in an amount of 100 mls. conc. $H_2SO_4$ per 50 kgs. glycerol.

The presently perferred entraining liquid is toluene but other entraining liquids which boil above 100°C, e.g. chlorobenzene, may be used. It is known generally to use entraining liquids in esterification reactions but previously the boiling points of such liquids have not proved to be critical. In the method of the present invention however, it is essential that the entraining liquid should have its boiling point above 100°C. The entraining liquid removes the water formed during esterification from the reaction mixture by azeotropic distillation maintained by heating the reaction mixture to a temperature above 100°C, for example by heating on an oil bath.

The esterification product may be separated into its mono- and di-ester components but usually will be used without such separation. The esters are known compounds and are useful primarily as chemical intermediates. As reported above, a particular use for esterification products derived from p-nitrobenzoic acid and having a high mono-ester content is as an intermediate in the preparation of glycerol mono-p-aminobenzoate.

Commercial grade glycerol mono-p-aminobenzoate presently is prepared by the controlled esterification of p-aminobenzoate with glycerol and is a semisolid, waxy mass or syrup (see Merck Index, Eighth Edition, 1968). It is a mixture of approximately 80% of the mono-terminal glycerol ester and 20% of the di-terminal glycerol ester and is used in cosmetic sunscreening and the like preparations.

The di-ester is less soluble than the mono-ester and tends to separate from the formulation. Unfortunately, separation of the esters in the esterification product is uneconomic. Other methods described in the literature first prepare by one of the prior art methods supra glycerol mono-p-nitrobenzoate which then is reduced to the glycerol mono-p-aminobenzoate. Such other methods provide routes for obtaining a product of low di-ester content but the relatively high cost of the indirect esterification methods has militated against commercial scale operation.

In contrast to the prior art methods of preparing glycerol mono-p-aminobenzoate, reduction of the esterification product of the preferred embodiment of this invention provides at commercially acceptable cost a product eminently suitable for use as a sunscreening agent. This product contains 10% or less of glycerol di-p-aminobenzoate and is obtained in the form of a white powder melting at approximately 114°C. The reduction may be carried out by any of the well known methods for reducing aromatic nitro compounds to aromatic amines, e.g. using iron in water containing a little hydrochloric acid.

The following Examples 1 to 4 illustrate methods in accordance with the present invention, whilst Example 5 illustrates the preparation of glycerol mono-p-aminobenzoate from the product of Example 1. All temperatures are in degrees centigrade.

EXAMPLE 1

2080 Gms glycerol and 420 mls of toluene were placed in a 5 liter vessel equipped with a stirrer, reflux condenser and a water separator. The mixture was stirred and heated under reflux until water ceased to separate in the separator. The mixture was allowed to cool, and 834 gms p-nitrobenzoic acid added (molar ratio glycerol : nitrobenzoic acid = 4.6:1). The heating and stirring were recommenced until the toluene began to reflux. Five mls concentrated sulphuric acid were then added to the mixture over 15 minutes. The refluxing was continued until 87 mls of water had been collected in the water separator. Heating and stirring were stopped and the mixture was allowed to separate into two layers.

The lower layer was separated and run into a cold stirred solution of 62.5 gm sodium bicarbonate in 21 liters of water, and the stirring continued until the product solidified. It was then collected in a filter, washed with water, and dried in a vacuum oven. The yield of glycerol mono-p-nitrobenzoate containing a small proportion of glycerol di-p-nitrobenzoate was 1 kg.

EXAMPLE 2

23 Gms (0.25 mole) glycerol, 42 gms (0.25 mole) p-nitrobenzoic acid, and 100 mls toluene were stirred and heated under reflux in a 500 ml flask fitted with a water separator, until no more water separated in the separator. 0.25 ml concentrated sulphuric acid was added and refluxing continued until a further 4.5 mls of water had separated. The toluene was then distilled off under reduced pressure on the water bath, and the residue poured into a solution of 25 gms sodium bicarbonate in 825 mls water. The mixture was stirred for 6 hours, filtered and the residue washed with distilled water and then dried in a vacuum oven.

The experiment was repeated using 46, 69, 100, 150 and 200 gms of glycerol.

The proportion of mono and di-esters present in each sample was measured by determining the % glycol content, using the periodate method. The results are given in the following table.

| Molecules of glycerol per molecule of p-nitrobenzoic acid | Di-ester content | Yield |
| --- | --- | --- |
| 1 | 42% | 59.4% |
| 2 | 36% | 56.6% |
| 3 | 10% | 62.5% |
| 4.3 | 2% | 71.6% |
| 6.6 | 1% | 76.7% |
| 8.7 | 0% | 72.6% |

EXAMPLE 3

42 Gms p-nitrobenzoic acid, 100 gms glycerol (molar ratio glycerol : nitrobenzoic acid 4.3:1) and 100 mls chlorobenzene were heated under reflux with stirring in a 500 ml flask fitted with a water separator until no further separation of water was observed. 0.25 ml concentrated sulphuric acid was then added and refluxing continued until a further 4.5 mls water had been separated. The chlorobenzene was distilled off under reduced pressure on the water bath. The residue was poured into a cold solution of 25 gms sodium bicarbonate in 825 mls water, and stirred for 4 hours.

The product was filtered off, washed with distilled water and dried in the vacuum oven. The yield of glycerol mono-p-nitrobenzoic containing a small proportion of glycerol di-p-nitrobenzoate was 30.1 gms (50%).

EXAMPLE 4

Example 3 was repeated using 100 mls toluene and 1 gm toluene sulphonic acid in place of the chlorobenzene and sulphuric acid. The yield was 41 gms (67.1%).

EXAMPLE 5

1 kg of glycerol p-nitrobenzoate mixture obtained by the method of EXAMPLE 1 was added in portions to a stirred mixture of 700 gms iron powder (150 mesh), 2 liters of water and 10 mls of concentrated hydrochloric acid initially at 60° so that the temperature did not exceed 90°. After the addition was complete, the mixture was stirred for a further one-half hour at 80°.

The pH of the mixture was then adjusted to pH 9 by addition of solid sodium carbonate, and the mixture was filtered at 80°. The pH of the filtrate was adjusted to pH 6.8 by addition of solid sodium metabisulphite. On cooling the filtrate so treated, glycerol mono-p-aminobenzoate containing a small proportion of glycerol di-p-aminobenzoate separated and was collected, washed with cold water, and dried in a vacuum oven. Yield 650 gms (74%) of a white powder melting at 114°.

We claim:

1. In the known method of esterifying a nitrobenzoic acid with glycerol by heating a mixture of the nitrobenzoic acid and glycerol in the presence of (a) a catalytic quantity of an acid esterification catalyst which is soluble in the reaction mixture at the reaction temperature and (b) of an entraining liquid to separate liberated water by azeotropic distillation, the improvement comprising the combination of using an entraining liquid having a boiling point above 100°C and heating the reaction mixture to a temperature above 100°C.

2. The method according to claim 1 wherein the esterification catalyst is sulphuric acid or a toluene sulphonic acid.

3. The method according to claim 1 wherein the entraining liquid is toluene or chlorobenzene.

4. The method according to claim 1 wherein the molar ratio of glycerol to nitrobenzoic acid in the reaction mixture is at least 3:1.

5. The method according to claim 4 wherein the molar ratio is about 4:1.

6. A method of preparing glycerol mono-para-nitrobenzoate comprising heating at a temperature of at least 100°C a mixture of glycerol and para-nitrobenzoic acid in a molar ratio of at least 3:1 in the presence of (a) an acid esterification catalyst which is soluble in the reaction mixture at the reaction temperature and (b) an entraining liquid having its boiling point above 100°C to separate liberated water by azeotropic distillation.

7. The method according to claim 6 wherein the esterification catalyst is sulphuric acid or a toluene sulphonic acid.

8. The method according to claim 6 wherein the entraining liquid is toluene or chlorobenzene.

9. The method according to claim 6 wherein the molar ratio is about 4:1.

* * * * *